United States Patent
Bittar et al.

(10) Patent No.: US 9,733,191 B2
(45) Date of Patent: Aug. 15, 2017

(54) DIRECTING A DRILLING OPERATION USING AN OPTICAL COMPUTATION ELEMENT

(75) Inventors: Michael S. Bittar, Houston, TX (US); Clive D. Menezes, Houston, TX (US); Christopher Michael Jones, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 595 days.

(21) Appl. No.: 14/357,496

(22) PCT Filed: Nov. 15, 2011

(86) PCT No.: PCT/US2011/030728
§ 371 (c)(1),
(2), (4) Date: May 9, 2014

(87) PCT Pub. No.: WO2013/074089
PCT Pub. Date: May 23, 2013

(65) Prior Publication Data
US 2014/0311803 A1 Oct. 23, 2014

(51) Int. Cl.
*G01N 21/84* (2006.01)
*G01N 21/59* (2006.01)
(Continued)

(52) U.S. Cl.
CPC .............. *G01N 21/84* (2013.01); *E21B 44/00* (2013.01); *E21B 47/0002* (2013.01); *E21B 47/123* (2013.01); *G01N 21/59* (2013.01)

(58) Field of Classification Search
CPC .......... E21B 7/04; E21B 47/00; E21B 47/024; E21B 44/00; E21B 47/123; G01B 7/30;
(Continued)

(56) References Cited

U.S. PATENT DOCUMENTS 5,898,517 A * 4/1999 Weis ..................... E21B 47/123
356/32
6,206,108 B1 * 3/2001 MacDonald ............ E21B 44/00
175/24
(Continued)

FOREIGN PATENT DOCUMENTS

EP 2317068 A1 5/2011
RU 2230343 C2 6/2004
(Continued)

OTHER PUBLICATIONS

"Chinese Application Serial No. 201180074866.1, Response filed Apr. 19, 2016 to Office Action dated Dec. 4, 2015", (w/ English Translation of Amended Claims), 30 pgs.
(Continued)

*Primary Examiner* — David Porta
*Assistant Examiner* — Faye Boosalis
(74) *Attorney, Agent, or Firm* — Gilliam IP PLLC

(57) ABSTRACT

Various embodiments include apparatus and methods to operate a tool downhole in a well, where the tool has an optical computation element to determine different properties of downhole structures. Such an optical computation element can be structured to provide optical analysis of fluid and material composition of the downhole environment associated with a drilling operation. The data measurements from the optical computation element can be used in a geosteering operation. Additional apparatus, systems, and methods are disclosed.

32 Claims, 6 Drawing Sheets

(51) Int. Cl.
*E21B 44/00* (2006.01)
*G01V 8/00* (2006.01)
*E21B 47/00* (2012.01)
*E21B 47/12* (2012.01)

(58) Field of Classification Search
CPC .......... G01N 21/84; G01N 21/59; G01V 8/00; G01V 8/10; G01V 8/16; G01V 8/22; G01V 8/20; G01V 11/00
See application file for complete search history.

(56) References Cited

U.S. PATENT DOCUMENTS

| | | | |
|---|---|---|---|
| 7,697,141 | B2 | 4/2010 | Jones et al. |
| 8,347,985 | B2 | 1/2013 | Bittar et al. |
| 2009/0199630 | A1 | 8/2009 | DiFoggio et al. |
| 2010/0153048 | A1 | 6/2010 | Myrick et al. |

FOREIGN PATENT DOCUMENTS

| | | |
|---|---|---|
| WO | WO-2006063094 A1 | 6/2006 |
| WO | WO-2008087477 A1 | 7/2008 |
| WO | WO-2010014265 A1 | 2/2010 |
| WO | WO-2011022012 A1 | 2/2011 |
| WO | WO-2011022020 A1 | 2/2011 |
| WO | WO-2011063086 A1 | 5/2011 |
| WO | WO-2011112185 A1 | 9/2011 |
| WO | WO-2013074089 A1 | 5/2013 |

OTHER PUBLICATIONS

"Russian Application Serial No. 2014122122, Response filed Apr. 5, 2016 to Office Action dated Dec. 21, 2015", (w/ English Translation), 14 pgs.
"Australian Application Serial No. 2011381034, Response filed Dec. 15, 2015 to First Examiners Report mailed May 13, 2015", 18 pgs.
"Canadian Application Serial No. 2,854,443, Amendment filed Nov. 16, 2015 in response to Office Action mailed Jun. 3, 2015", 26 pgs.
"Chinese Application Serial No. 201180074866.1, Office Action mailed Dec. 4, 2015", (w/ English Translation), 16 pgs.
"Russian Application Serial No. 2014122122, Office Action mailed Dec. 21, 2015", (w/ English Translation), 10 pgs.
"Australian Application Serial No. 2011381034, First Examiners Report mailed May 13, 2015", 3 pgs.
"European Application Serial No. 11788298.5, Response filed Jan. 8, 2015 to Office Action mailed Jul. 18, 2014", 12 pgs.
"International Application No. PCT/US2011/060782, Response and Amendment filed Aug. 6, 2013 to Written Opinion mailed Jul. 17, 2012", 7 pgs.
"Canadian Application Serial No. 2,854,443, Office Action mailed Jun. 3, 2015", 5 pgs.
"European Application Serial No. 11788298.5, Office Action mailed Jul. 18, 2014", 2 pgs.
"international Application No. PCT/US2011/060782, Response filed Jan. 8, 2014 to Written Opinion mailed Nov. 8, 2013", 8 pgs.
Myrick, M. L., et al., "Application of multivariate optical computing to simple near-infrared ponit measurements", *Instrumentation for Air Pollution and Global Atmospheric Monitoring Proceedings of SPIE vol. 4574*, (2002), 208-215.
"International Application No. PCT/US2011/060782, Written Opinion mailed Jul. 17, 2012", 5 pgs.
"International Application Serial No. PCT/US2011/060782, International Preliminary Report on Patentability mailed Feb. 7, 2014", 6 pgs.
"International Application Serial No. PCT/US2011/060782, International Search Report mailed Jul. 17, 2012", 4 pgs.
"International Application Serial No. PCT/US2011/060782, Written Opinion mailed Nov. 8, 2013", 6 pgs.
"Russian Application Serial No. 2014122122, Office Action mailed Apr. 22, 2016", (w/ English Translation), 10 pgs.

\* cited by examiner

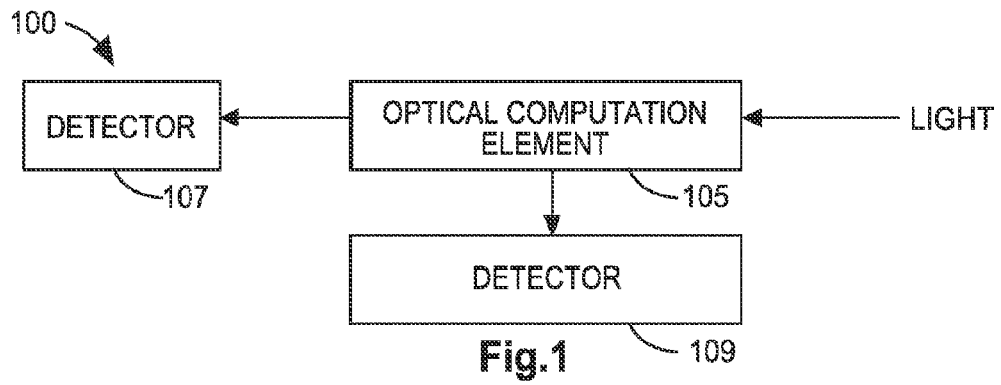
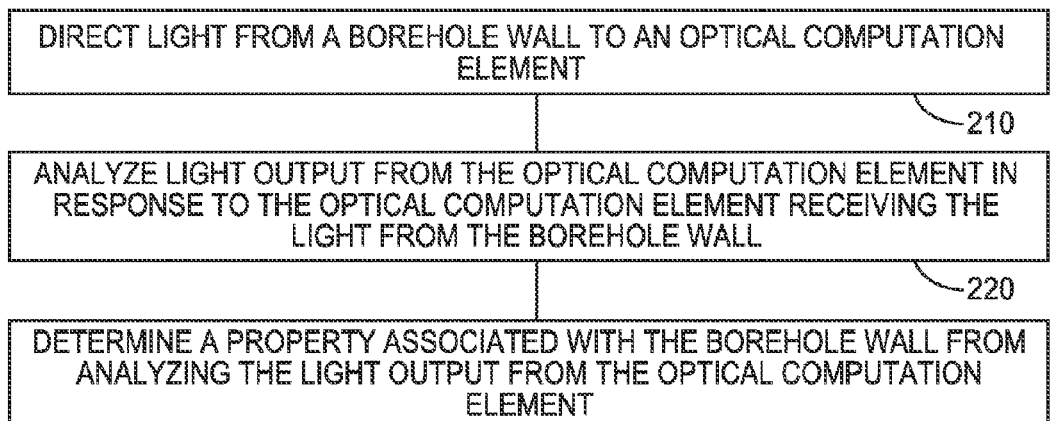
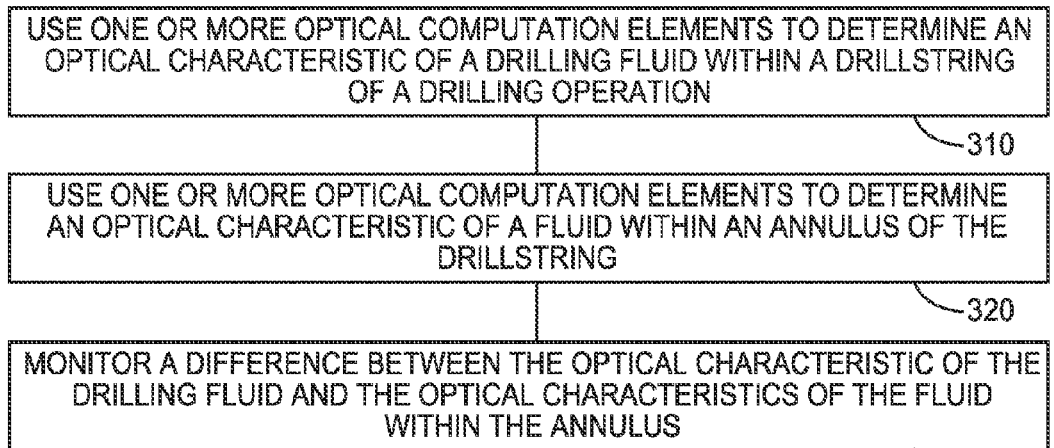

DIRECTING A DRILLING OPERATION USING AN OPTICAL COMPUTATION ELEMENT

TECHNICAL FIELD

The present invention relates generally to apparatus for making measurements related to oil and gas exploration.

PRIORITY APPLICATION

This application is a U.S. National Stage Filing under 35 U.S.C. 371 from International Application No. PCT/US2011/060782, filed on 15 Nov. 2011, and published as WO 2013/074089 A1 on 23 May 2013; each of the application and publication is incorporated herein by reference in its entirety.

BACKGROUND

In drilling wells for oil and gas exploration, understanding the structure and properties of the associated geological formation provides information to aid such exploration. Optimal placement of a well in a hydrocarbon-bearing zone (the "payzone") usually requires geosteering with deviated or horizontal well trajectories, since most payzones extend in the horizontal plane. Geosteering is an intentional control to adjust drilling direction. An existing approach based on geosteering in well placement includes intersecting and locating the payzone followed by moving the drill string to a higher position and beginning to drill a new branch that approaches to the target zone from top. This first approach is time consuming, where drilling needs to be stopped and a device for branching needs to be lowered into the well. Another existing approach based on geosteering in well placement includes intersecting and locating the payzone followed by continuing drilling to approach the well from the bottom. This second approach can result in overshoot of the well path from the desired target zone and may only be effective if the well is highly deviated at point of intersection.

BRIEF DESCRIPTION OF THE DRAWINGS

FIG. 1 shows a block diagram of an example apparatus having an optical computation element for operation downhole in a well, in accordance with various embodiments.

FIG. 2 shows features of an example method of determining a property in a borehole using an optical computation element, in accordance with various embodiments.

FIG. 3 shows features of an example method using an optical computation element in a drilling operation, in accordance with various embodiments.

DETAILED DESCRIPTION

Figure 4:
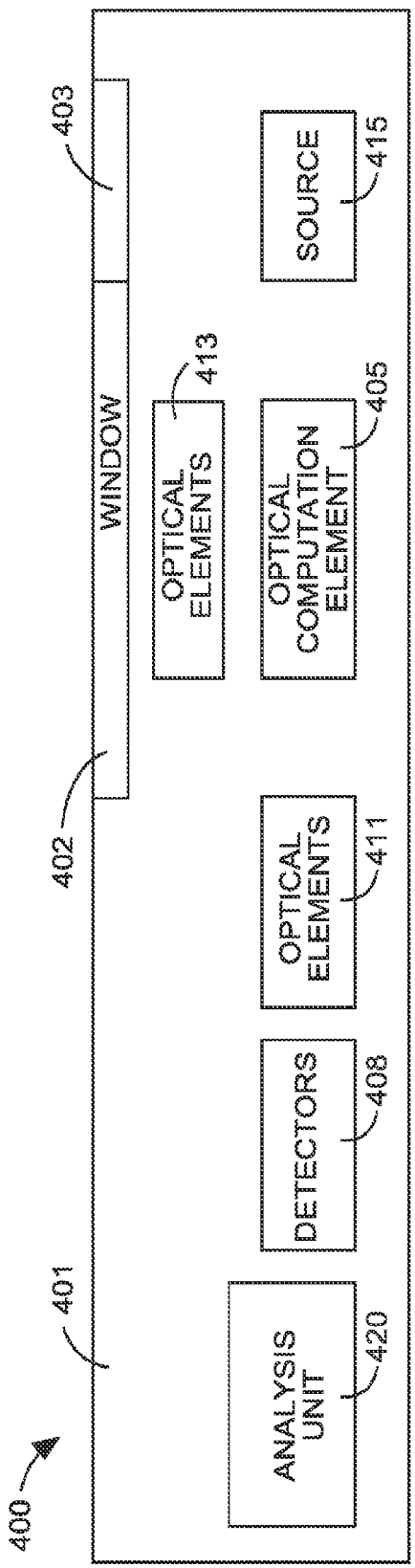
FIG. 4 shows a block diagram of an example system using an optical computation element operable in a drilling operation, in accordance with various embodiments.

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In various embodiments, an optical computation element can be arranged to operate in a downhole environment to provide optical analysis of fluid and material composition of the downhole environment associated with a drilling operation. An example of an optical computation element is a multivariate optical element (MOE). An optical computation element, arranged in a device or system to provide operational functionality with other components, may be referred to as an integrated computational element. An example of the principles of MOE operation can be found in Myrick, Soyami, Schiza, Fan, Haibach, Greer, Li and Priore, "Application of multivariate optical computing to simple near-infrared sample point measurements", Proceedings of SPIE vol. 4574 (2002). Light from a light source can pass through a sample, or reflect off the sample, and be partially transmitted and reflected from the MOE, which includes an interference filter. The difference between the transmitted and reflected light spectra is $S(\lambda)L(\lambda)$, where $S(\lambda)$ is the spectrum of light from the sample and $L(\lambda)$ is the spectral characteristic that the MOE is designed to provide. Since detectors measure intensity, the measured difference is the integral of $S(\lambda)L(\lambda)d\lambda$ over the bandwidth of the system. When the MOE spectral characteristic $L(\lambda)$ is chosen to provide a measurement of a specific substance, the output of the system provides a relative measure of that substance's concentration. Multiple MOEs can be used to test for different substances. An example of multivariate optical elements for an optical analysis system can be found in U.S. Pat. No. 7,911,605. In addition, one approach to MOE design, including techniques for nonlinear calibration, can be found in U.S. Patent Application Publication 2010/0153048.

A MOE is an optical computation element that may be viewed as an analog computer, which uses light, to perform only one computation. A MOE can be arranged such that it adds, subtracts, multiplies, and divides. It is noted that addition, subtraction, multiplication, and division are operations that can be used to perform what is called a regression. A regression is typically an inversion process to extract information, which is specific data, from a broader form of data. When light (electromagnetic radiation) interacts with matter, in whatever form the matter has, the chemical and physical characteristics of the matter, which are optically active, effectively encodes itself into that light. MOEs can be designed essentially as optical processors with regression vectors to extract the relevant data of the matter interacting with light.

MOEs that perform a computation in the optical domain can be constructed in a manner similar to construction of an optical filter. Optical filters can be constructed as an interference filter, an absorption filter, a holographic filter, or other form of filter of electromagnetic radiation. An optical filter is typically designed to pass or reject a specific band of light, where a band is generally a continuous subset of light. For example, an optical filter can be realized as a Gaussian filter, a cut-off filter, a broadband filter, or other type of filter structured with respect to one or more continuous ranges of frequencies (wavelengths) of light such that the filter transmits, or rejects, light with respect to these frequencies. An optical filter, in general, has a specific transmissive characteristic such that it transmits or rejects a certain amount of light over a range of frequencies that can be referred to as the width of the band. The output of these filters is light at selected frequencies, whose total intensity can be detected. However, unlike filters, a MOE can provide more extractible data than the total intensity of light that is passed.

Using filter construction techniques, a regression vector can be encoded into the filter forming an MOE. The encoded regression vector uses the interference properties of light. Light can interfere with itself, providing positive or negative interference. This positive and negative inference allows for a mathematical calculation on the light itself. With a regression vector encoded into the optical filter, as light passes through the encoded optical filter, a calculation is performed. An encoded filter in such a configuration is no longer a filter in the conventional sense of the filter. In addition, by encoding a pattern recognition or a dot-product regression vector into the filter forming the MOE, information can be extracted from the optical stream to the MOE at a much higher resolution than the bandwidth of the MOE. Since the transmission and absorption properties of materials are typically wavelength dependent, an optical computation element can be arranged with respect to other optical components that provide to light to the optical computation element in a selected range of wavelengths.

In various embodiments, an optical computation element, such as a MOE, can be arranged to operate downhole in a well. Optical computation elements structured as part of a drilling tool can be used for a variety of applications including, but not limited to, extraction of physical and/or chemical information about the well bore, extraction of physical and/or chemical information about fluids in the well bore, application of the extracted information to monitor the safety of a drilling operation, and application of the extracted information for steering a drill bit in a drilling operation. To collect information about the well bore, light from an interaction with the well bore can be passed through an optical computation element, which is designed to examine a property of the well bore under investigation. With the light interacting with the optical computation element, the light has been mathematically operated on by this optical computation element. The output from the optical computation element can be passed to an optical detector. The signal output from the optical detector is specifically related to the answer from the query made by the encoded optical computation element. For example, the signal output from the optical detector can be specifically related to an estimation of the property of the well bore or the fluids in the wellbore. The property can include, but is not limited to, concentration of the analytes of the wellbore or fluids. The output of the detector may be directly proportional to the property being investigated. The output may differ from direct proportionality due to such factors as slight non-linearities of the detector or the calibration of the system may not be perfectly linear. For example, if a slightly non-linear calibration is encoded into MOE, then the output light might be slightly non-linear as well. Due to these variations, the signal output from the detector is an estimation of the property under investigation. However, the signal output may be directly related to the property under investigation.

The property under investigation may include, among other properties, composition of the wellbore, fluid composition, fluid composition at the contact with the well bore surface, or the porosity of the wellbore. The property under investigation can include relative concentrations of different materials associated with a drilling operation. For example, when examining a reservoir section, an optical computation element can provide data with respect to relative concentrations of such materials as sand, a carbonate, and clay in the section. This data can provide information on the quality of the reservoir section, where the quality is based on materials present in the section. The quality analysis can be made with respect to fluids such as oil and water. In addition, data provided by the optical computation element can be used to steer a drilling operation away from a water section or towards an oil section.

FIG. 1 shows a block diagram of an embodiment of an apparatus 100 having an optical computation element 105. Light can be directed to optical computation element 105, which can be arranged such that a portion of light passes through optical computation element 105 to detector 107 and a portion of the light is reflectively directed from optical computation element 105 to detector 109. The light directed to optical computation element 105 can the result of an interaction of material under investigation. The interaction may be realized with light transmitted through the material, light reflected from the material, light emitted from the material, or light scattered from the material. For transmission or reflection from the material, the light can be provided to the material by a source incorporated in apparatus 100. Apparatus 100 can also include other optical components such as filters and beamsplitters to provide the light to optical computation element 105 that can be limited to a wavelength range correlated to the material under investigation.

FIG. 2 shows features of an embodiment of a method of determining a property in a borehole using an optical computation element. At 210, light from a borehole wall is directed to an optical computation element. A probe light can be directed at the borehole wall such that redirection of the probe signal from the borehole wall provides the light directed from the borehole wall to the optical computation element. The probe light can be generated using a probe device such that the probe device physically contacts the borehole wall, where the probe light passes from the probe device to the borehole wall. Material can be scraped off from the borehole wall using the probe device. The material scrapped off can include some of the filter cake that naturally builds up on the wellbore. Removing such material provides a mechanism to reflect light from the interface of the optical probe and the wellbore. This process yields data about this interface. In various embodiments, sapphire, zinc sulfite, a diamond, or silicon carbide can be used as materials for the optical probe device. These are hard materials that can both serve as an optical conduit to the wellbore and as a method of removing the filter cake. The use of these materials can be correlated with the selection of an optical source such that the wavelength is optically transparent in certain optical regions for the selected material for the probe device. The probe light can be also generated by transmitting the probe light from a source, disposed in a tool containing the optical computation device, through a fluid to the borehole wall.

In an embodiment, an optical conduit for probe light propagating between the tool containing the optical computation device and the wellbore can be formed using drilling fluid. A portion of the drilling fluid flowing down the center of the drillstring can be tapped near the location of the tool such that the tapped portion of the drilling fluid flows between the tool and the wellbore wall. This tapped drilling fluid provides the conduit through which light can propagate between the wellbore wall and the tool. The drilling fluid provides a relatively transparent medium that is substantially free of solids, since the drilling fluid in this portion of its flow pattern in the drilling operation has been provided substantially free of solids. This formed conduit allows examining the wellbore wall without a probe contacting the wellbore wall.

At 220, light output from the optical computation element in response to the optical computation element receiving the light from the borehole wall is analyzed. At 230, a property associated with the borehole wall is determined from analyzing the light output from the optical computation element. Based on the determined property, a signal can be generated to direct a drilling operation. Generating the signal to direct the drilling operation can include geosteering the drilling operation. Geosteering the drilling operation can include maintaining the borehole within a reservoir pay zone. Generating the signal to direct the drilling operation can include generating a monitoring signal to provide advanced warning with respect to a safety condition of the drilling operation.

Determination of a property associated with the borehole wall can include determining one or more of a porosity of the borehole wall, a composition of the borehole wall, or a formation fluid measurement corresponding to the borehole wall. In addition, values of the property associated with the borehole wall can be determined as the tool, on which the optical computation device is disposed, moves along a length of the borehole. A two-dimensional map of the borehole wall can be generated from these values. In addition, contamination within a drilling fluid from the drilling action can be monitored from analyzing the light output from the optical computation element with respect to a frequency of light, in the light directed to the optical computation element, at which the drilling fluid is transparent.

FIG. 3 shows features of an embodiment of an example method using an optical computation element in a drilling operation. At 310, one or more optical computation elements are used to determine an optical characteristic of a drilling fluid within a drillstring of a drilling operation. In an embodiment, only one optical computation element is used to determine an optical characteristic of a drilling fluid within a drillstring of a drilling operation. At 320, the one or more optical computation elements are used to determine an optical characteristic of a fluid within an annulus of the drillstring. The annulus is the space between two objects, such as between the wellbore and casing, where the casing is a pipe disposed in the wellbore, between casing and tubing, or between drillstring and wellbore wall.

At 330, a difference between the optical characteristic of the drilling fluid and the optical characteristic of the fluid within the annulus is monitored. The method can include measuring fluids leaking into a formation due to drilling at a drill bit location in the drilling operation. Based on monitoring the difference between the optical characteristic of the drilling fluid and the optical characteristic of the fluid within the annulus, a property associated with the fluid within the annulus can be determined. A signal can be generated to direct a drilling operation based on the determined property. Generating the signal to direct the drilling operation can include geosteering the drilling operation or generating a monitoring signal to provide advanced warning with respect to a safety condition of the drilling operation.

FIG. 4 shows a block diagram of an embodiment of an example system 400 using an optical computation element 405 operable in a drilling operation. Optical computation element 405 is disposed in a housing 401, where housing 401 is attachable to a drillstring. A window 402 in housing 401 can be arranged to receive light from exterior to housing 401 such that the light is directed from a region, exterior to the drillstring, to optical computation element 405 when housing 401 is mounted on the drillstring. An analysis unit 420 can be structured to provide a signal based on an output from optical computation element 405 in response to optical computation element 405 receiving the light from exterior to the drillstring, where the signal is provided from analysis unit 420 to direct a drilling operation based on a property of the region determined from the output from optical computation element 405. System 400 can also include an optical source 415 to generate light that is reflected from exterior to the housing such that the reflected light provides the received light directed to optical computation element 405. System can also include an additional window 403 structured such that the generated light by the optical source 415, with optical source 415 disposed in housing 401, exits housing 401 to reflect from exterior to housing 401.

Windows 402 and 403 can consist of a material that is transparent at the desired wavelengths of operation for optical computation element 405. The material selected for windows 402 and 403 may be a hard material such as sapphire. Other transparent materials that have hardness characteristics for use downhole can include silicon carbide or other hard materials that provide optical transparency for the selected application.

System 400 can include optical detectors 408 arranged relative to optical computation element 405 to detect light directed from optical computation element 405 to the respective optical detector. The arrangement of optical detectors 408 can be coupled with analysis unit 420 to provide signals to analysis unit 420. An analysis unit 420 can be structured to determine a difference between a drilling fluid within a drillstring of a drilling operation and a fluid within an annulus of the drillstring based on the signals. System 400 can also include optical elements 411 to direct light from optical computation element 405 to optical detectors 408. Optical elements 411 can include one or more optical components such as lenses, filters, or beamsplitters. System 400 can also include optical elements 413 to direct light to optical computation element 405 from window 402. Optical elements 413 can include one or more optical components such as lenses, filters, or beamsplitters.

Figure 5:
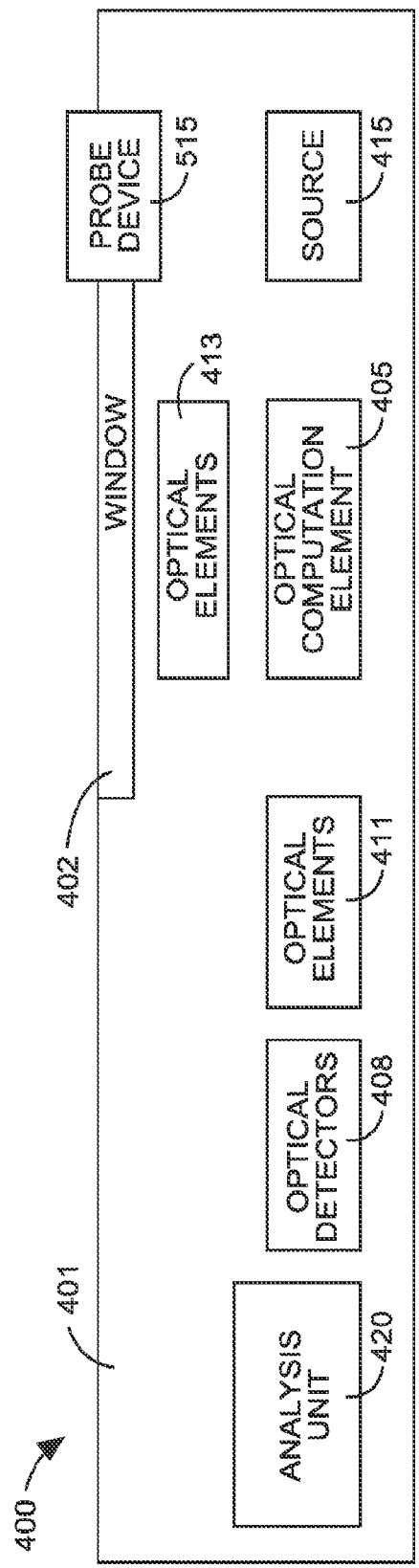
FIG. 5 shows the example system of FIG. 4, where a probe device is physically arranged on the housing to contact a borehole wall, in accordance with various embodiments.

FIG. 5 shows system 400 structured with a probe device 515 physically arranged on housing 401 to contact a borehole wall. Probe device 515 can be structured to generate a probe light, with probe device 515 physically arranged on housing 401 to contact a borehole wall, such that probe light passed from probe device 515 to the borehole wall provides the received light from exterior to housing 401 directed towards optical computation element 405. Probe device 515 can be structured as conduit to transit light from source 415 outward from housing 401. Probe device 515 can be structured to be operable to scrap off material from the borehole wall. Sapphire, zinc sulfite, diamond, or silicon carbide can be used as materials for probe device 515. These are hard materials that can both serve as an optical conduit to the wellbore wall and as a structure to remove filter cake from the wellbore wall. The use of these materials can be correlated with the selection of the optical source such that the wavelength is optically transparent in certain optical regions for the selected material of probe device 515.

Probe device 515 can be realized using a pad pressed firmly against the borehole wall. Using the pad, fluid can be withdrawn from the formation into the wellbore, which clears out the filter cake and provides a clear fluid path to the formation. The clear fluid path provides an optical conduit to direct light from source 415 to the borehole wall. The fluid may be water, oil, gas, or combinations thereof. The quality of the optical conduit depends on the type of fluid withdrawn using the pad. Alternatively, rather than withdrawing fluid from the formation to provide an optical conduit, the pad can be flushed with a designed optically transparent fluid. To effectively scrap off the material from the wellbore wall, probe device 515 may also be realized by pressing a snorkel-like device an inch or so into the wellbore. The pressing activity can be conducted by hydraulically placing about 10,000 to 20,000 psi onto the snorkel that presses it into the wellbore.

In various embodiments, an optical computation element, such as a multivariate optical element, can be used in geosteering applications. When incorporated into a logging-while-drilling (LWD) tool, MOEs can provide measurements of borehole wall composition including boundaries, fractures, and formation fluid measurements. These measurements can be converted into a borehole wall map to enable drillers to visualize the downhole situation. Information from processing MOE data can be combined with other information to decide in which direction to steer the borehole. This other information can include information regarding the drilling operation that includes data from regions away from the drilling location near which the MOE-based tool is located. Since data from a MOE-based tool is collected from regions within close proximity, this other information essentially provides a bigger picture of the drilling operation. In addition, information from processing MOE data can be incorporated into electronic control systems to direct the drilling operation autonomously such that activities of drillers can be directed to monitoring the geosteering along with overall regulation of the drilling operation.

Figure 6:
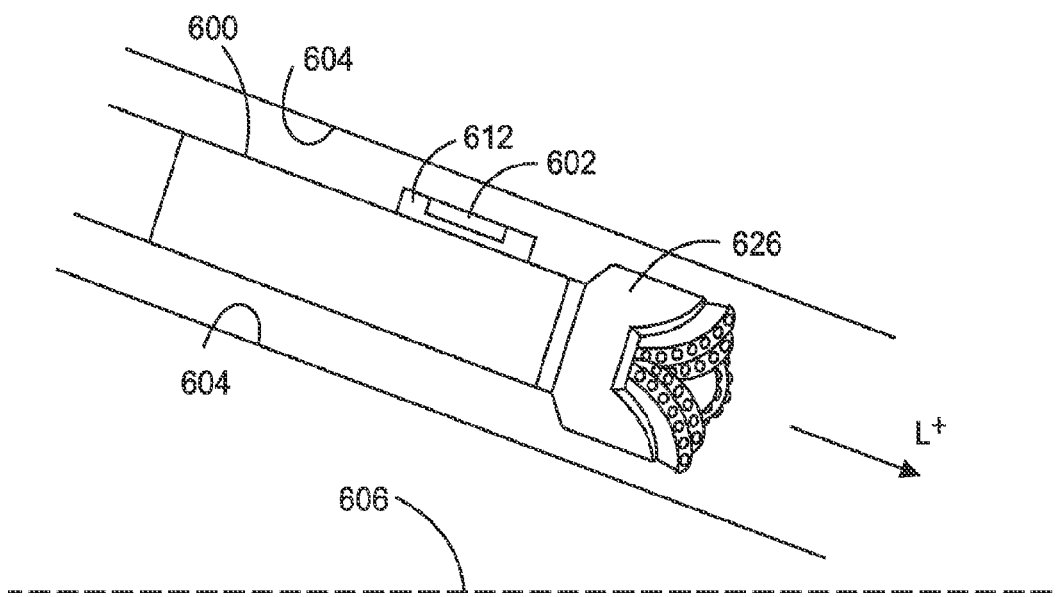
FIG. 6 illustrates a block diagram of an example logging while drilling tool having a window through which light can be reflected off a borehole wall, in accordance with various embodiments.

FIG. 6 illustrates a block diagram of an embodiment of an example logging while drilling tool 600 having a window 602 through which light can be reflected off a borehole wall 604. Drilling tool 600 can be located in a pressure housing behind drill bit 626. As shown in FIG. 6, drill bit 626 is being directed into bedding plane 606 in the $L^+$ direction. Window 602 can be positioned to minimize effects of borehole fluids. For example, window 602 can be positioned on a stabilizer blade 612 or some other protrusion from the body of drilling tool 600. Window 602 can be inset such that window 602 is protected from abrasion. Window 602 can also be protected from abrasion by guard structures of some form. Such guard structures can be used with window 602 inset or without window 602 inset. Window 602 can be very small, e.g., the size of a fiber-optic terminus. Illumination of a borehole wall 604 can be provided through the window 602 or through a separate window. As drilling progresses, path of window 602 traces a tight spiral along the borehole wall 604, enabling tool measurements to provide a two-dimensional (2D) map of the borehole wall characteristics as indicated in FIG. 7.

Figure 7:
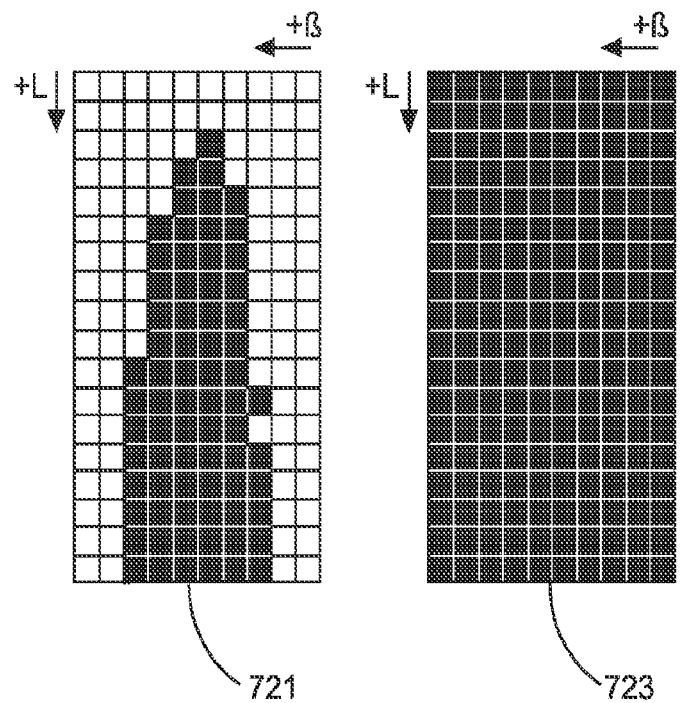
FIG. 7 shows signal logs at two different times relative to the operation depicted in FIG. 6 with respect to the tool as it rotates while moving in the drilling direction, in accordance with various embodiments.

FIG. 7 shows signal logs at two different times relative to the operation depicted in FIG. 6 with respect to tool 600 as it rotates while moving in direction $L^+$. A monitored signal 721 from window 602 provides at pattern at time $t_1$, while monitored signal 723 from window 602 provides a pattern at a later time $t_2$. As can be seen, the pattern is evolving from striking bedding plane 606 at an angle, indicated in 721 to being completely within the bedding zone, indicated in 721.

The data from the tool using an optical computation element, such as an MOE, can be used to determine and indicate that the drilling operation is within a target zone. Continuing processing of the data from the tool can be used to stay within a particular target zone, which may be an oil-bearing formation, for the drilling operation. If the region entered is not the target, the data from the tool can be used to continue drill laterally in the current direction for awhile until a target zone is reached or the data from the tool can be used to alter the direction of drilling. From the tool data, drilling direction can be altered to progress through soft shell in the area rather than nearby hard sandstone. In addition, steering using the tool is not necessarily solely for the purpose of sniffing and staying within a reservoir section, but can be used to determine the particular lithologic zone in which the tool is disposed.

Light reflected from a borehole wall can be processed by one or more optical computation elements, such as MOEs, to measure various formation characteristics. For example, processing of the reflected light by the optical computation elements can provide a measurement of concentration of hydrocarbon molecules and rock composition. A borehole wall map generated by processing that uses the optical computation elements can provide indications of reservoirs and boundaries penetrated by the borehole. An operator observing the map can make steering decisions such as, for example, decisions to keep the borehole within a reservoir pay zone. These decisions can include decisions to steer away from regions. Alternatively, results of the processing can be autonomously provided to an analysis unit of an automated system to determine parameters to use to conduct drilling operations. The automated system can include one or more processors, a memory system, and logic devices to compare the results with stored information that represents properties of pay zones. The stored information can include properties of regions to be avoided. The geosteering analysis can include an iterative process of evaluating the changes in the processed light with respect to the comparisons of the processed light with respect the stored information. Evaluation of these changes can provide a basis for making geosteering adjustments.

Measurement information from optical computation elements can be communicated with associated tool position and orientation information to a surface processing facility where it can be analyzed and presented to an operator for use in steering the borehole. Alternatively, downhole electronics can be structured to analyze data from the measurements of the optical computation elements along with other information to autonomously steer the borehole.

Tools, with optical computation elements such as MOEs, used to measure characteristics of a borehole wall can be structured to have the capability to essentially look through the wellbore fluid using light, at radiative energies transparent to the drilling fluid, that impinges on the borehole wall. The optical computation elements also can be structured to have the capability to monitor contamination within the drilling fluid. Such devices can be arranged to operate as either in a differential technique or as a direct measurement of the fluid in the annulus. A differential technique, for example, can include monitoring the difference between the optical characteristics of drilling fluid within the drill string to that in the borehole annulus. The arrangement of one or more optical computation elements, such as MOEs, allows measurements of fluids leaking into the formation via the drilling action at the bit. In a differential configuration for monitoring fluid properties, a single optical computation element can be used for monitoring "fresh drilling fluid" and annular fluid canceling out a significant amount of common mode variation.

During a drilling operation, formation fluid can invade the drilling fluid near the drill bit. Near the drill bit, the material of the drilling operation can include drilling fluid with a small portion of formation fluid that is influx into the wellbore with the drilling fluid. An approach to examining this relatively small amount of influx of formation fluid can include subtracting the effect of the drilling fluid itself. The drilling fluid itself, before the trace constituents are added by the drilling action, is essentially the material flowing through the annular pipe not far away from the drill bit. An indication of the drilling fluid without this trace constituent can be attained by examining the fluid that is flowing through the inside of the pipe. Thus, examining the fluid flowing through the inside of the pipe versus the fluid with the trace constituents from the formation on the outside of the pipe provides a differential measurement. Making a differential determination of fluids between what is inside and outside the drilling string generates a measurement of the formation fluid (trace constituents) with enhanced resolution. The enhanced resolution results from the large portion of the measurements that is common to the inside and outside being removed from the measurement. The differential measurement can be made with one or more optical computation elements.

Figure 8:
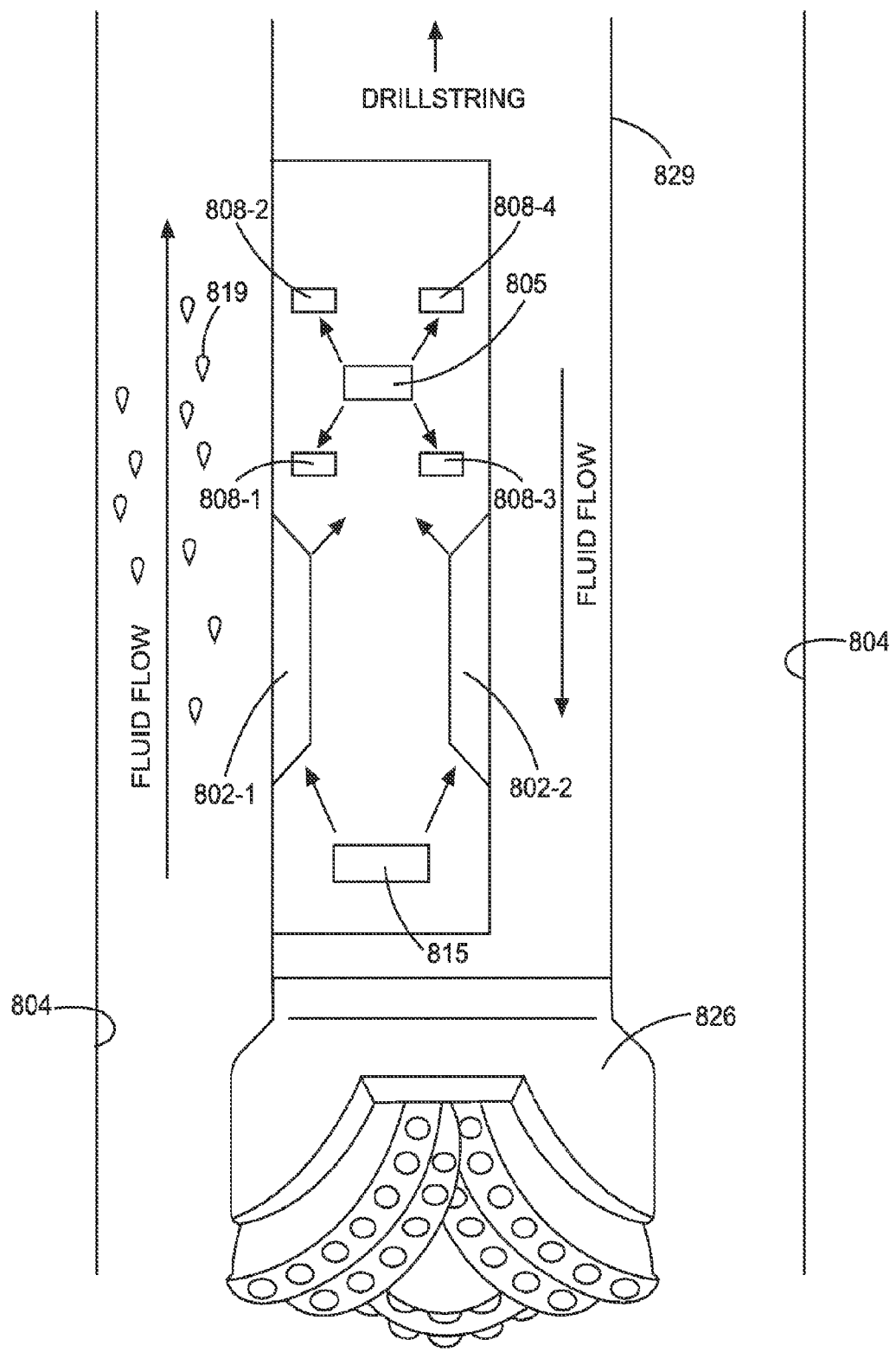
FIG. 8 shows a block diagram of an example arrangement of an optical computation element that examines drilling fluid flowing to and from a drill bit in a drilling operation, in accordance with various embodiments.

FIG. 8 shows an arrangement of an optical computation element 805 that examines drilling fluid flowing to and from drill bit 826 in a drilling operation. Optical computation element 805 can be arranged on a drill string 829 near drill bit 826 in a wellbore having wall 804. A source 815 provides light that is directed out window 802-2 towards the drilling fluid flowing towards drill bit 826. The drilling fluid flowing towards drill bit 826 can flow within the drill string 829. Source 815 can also provide light that is directed out window 802-1 towards the drilling fluid flowing back from drill bit 826 that can include constituents 819 from the formation. Alternatively, two different light sources can be used. A difference between the fluids flowing in the two directions is essentially constituents 819. A difference operation on measurement signals between the two directions can eliminate common factors that form the dominant portion of each individual measurement. This difference operation should provide data regarding constituents with higher resolution than measurements to determine constituents 819 directly as part of the fluid flow away from drill bit 826.

Light reflected from drilling fluid flowing towards drill bit 826 is received in window 802-2. Alternatively, window 802-2 can be arranged as two windows with one to transmit the light from source 815 and the other one to receive the light reflected from the drilling fluid flowing towards drill bit 826. Light reflected from drilling fluid flowing away from drill bit 826 is received in window 802-1. Alternatively, window 802-1 can be arranged as two windows with one to transmit the light from source 815 and the other one to receive the light reflected from the drilling fluid flowing away from drill bit 826. The light received in window 802-1 and the light received in window 802-2 are directed to optical computation element 805.

Optical computation element 805 can be arranged with four detectors 808-1, 808-2, 808-3, and 808-4, which can be referenced with respect to signals D1, D2, D3, and D4, respectively. Additional optical components can be used to direct and provide the appropriate light to optical computation element 805 and detectors 808-1, 808-2, 808-3, and 808-4. These additional optical components can include lenses, filters, and beamsplitters, which are not shown for ease of presenting the arrangement of optical computation element 805. Signals D1 and D3 are reflected from optical computation element 805 to their respective detectors 808-1 and 808-3, and signals D2 and D4 are transmitted through optical computation element 805 to their respective detectors 808-2 and 808-4. The difference between the transmissive signal and the reflected signal is directly related to the concentration of interest. A ratio of the respective properties can be formed as $(k_1D_1-k_2D_2)/(k_3D_3-k_4D_4)$, where $k_1$, $k_2$, $k_3$, and $k_4$ are fitting constants.

Although it is possible to monitor differences in fluid content at the surface using fluid measurements made at the surface, providing this service downhole provides operational enhancements. For example, steering decisions using a downhole MOE arrangement can be made immediately not delayed as compared with surface measurements. Delays with surface measurements include the transit time for cuttings and fluid to reach surface from the drill bit, where such transit time is typically ½ hour to 1 hour.

Using one or more MOEs arranged to make downhole measurements, the fluid emanating from the formation can be monitored for various compounds. For example, the MOE arrangement can be used to monitor for methane, which is one of the lightest components of petroleum and is likely to invade the wellbore. Upon detecting methane, the drill bit can be steered towards higher concentrations of methane.

Monitoring for compounds is not limited to methane. Compounds for which MOE-based monitoring includes propane, light hydrocarbons, and other compounds related to the particular drilling operation. The steering from analysis of the output of the downhole MOE device can be conducted based on a distribution, not just a single component. For example, if the MOE-based monitoring shows an increase in a ratio of methane to butane, this increase may indicate that the drilling is being directed into a gas cap, since the ratio of methane increasing relative to the concentration of butane indicates that a region enriched in gas components. For oil drilling steering, such indications can be used to direct the steering back out of this gas-enriched region back to the oil based reservoir section. The steering operation can be conducted maintain a distribution of light hydrocarbon components, such as but not limited to methane, ethane, propane, butane, pentane, and hexane, to appropriately place the well. Such steering of the drilling operation uses the chemical information from the downhole MOE arrangement that examines the constituents of the drilling fluid filtrate itself.

In contrast to monitoring fluids at the surface via a surface run fluid log, using an MOE downhole provides a sensor located closer to the drilling bit. At the surface, the constituents of the mud brought to the surface have spread transversely relative to the pipe as the fluid moves up the drillstring to the surface. Mud is drilling fluid that may include solids and other constituents from the drilling operation. Hence, a downhole MOE sensor arrangement located closer to the drill bit versus the surface run fluid log provides a measurement in which the drilling fluid examined has experienced less transverse dispersion for the sensor located closer to the drill bit. In addition, uphole the properties of the mud are only a proxy for the fluid downhole, whereas downhole the mud can be directly monitored before and after the drill bit and hence provide a differential of finer resolution. With less transverse dispersion, and finer resolution potential pay zones may be better identified.

Using an arrangement of an optical computation element, such as a MOE arrangement, downhole allows for better marking of a water oil contact point. This enhanced operation is provided because methane, which is much less soluble in water than hydrocarbons, can be detected by the optical computation element close to its location downhole. In addition, a downhole optical computation element can monitor for sharp rises of certain components before they reach the surface. For example, a downhole optical computation element can monitor for compounds such as $H_2S$ or methane, knowledge of which can allow "kicks or blowouts" to be mitigated before they occur. A kick is a flow of formation fluids into the wellbore during drilling operations. A blowout is an uncontrolled flow of reservoir fluids into the wellbore, and sometimes catastrophically to the surface. A blowout may consist of salt water, oil, gas, or combinations thereof. If kick or blowouts do occur, a downhole optical computation element can be structured such that a control system and/or drillers receive advanced warning of the kicks or blowouts.

A measurement arrangement using an optical computation element, such as a downhole MOE based measurement arrangement, can also be structured to monitor for such compounds as methane, ethane, $CO_2$, $H_2S$, or other volatile components. This monitoring provides a safety mechanism in that it can generate an early warning regarding the presence of these volatile compounds. For example, $H_2S$ typically reacts a way in the caustic mud such that it is not readily apparent that the drilling has gone through a reservoir section containing $H_2S$ based on the mud analysis at the surface.

A downhole MOE based measurement arrangement may be structured to monitor the volatile components in the mud of the drilling operation as the saturation point of the mud for those volatile components is approached. The properties of the drilling fluid with respect to saturation by gases such as how much gas can be dissolved in the mud before it goes two phase for a particular pressure and temperature are typically well understood. Since the MOE based measurement provides an analysis of chemical composition, the downhole MOE arrangement can be used to monitor for these gases to provide early kick detection. For example, with a downhole MOE arrangement providing the early kick detection indicating that two phase has just been broken down hole, appropriate actions can be taken at the surface. In addition, with the downhole MOE arrangement structured to monitor a rapidly increasing concentration of methane or volatile components, mitigating steps may be taken to prevent a kick from occurring. The arrangement of a MOE or other optical computation element as a downhole measurement tool, in accordance with arrangements as taught herein, may provide for the prevention of blowup scenarios.

In contrast to surface fluid measurement, downhole measurements using optical computation elements, such as MOEs, can provide immediate knowledge as to location with respect to a pay zone, or target zone. Such knowledge may be especially useful with respect to horizontal drilling to stay in a target zone. Optical computation element based information of a LWD tool can be combined with other "big picture" information to assist a drill rig operator in identifying and following desirable borehole pathways or to provide data to an automated system to identify and follow desirable borehole pathways. In various embodiments, geosteering can be performed based in whole or part on MOE measurements. The range of such measurements may be limited, and the borehole fluids may interfere with the reliability of such measurements. Nevertheless, such measurements offer a low power way to obtain high quality measurements of formation composition.

Figure 9:
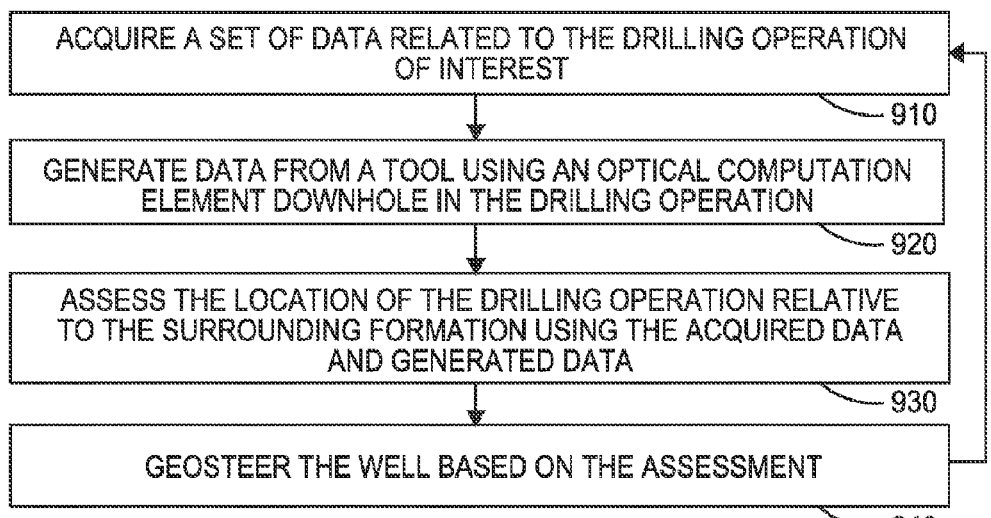
FIG. 9 shows features of an example method that includes using data from an optical computation element with other data in a geosteering procedure, in accordance with various embodiments.

FIG. 9 shows features of an embodiment of a method that includes using data from an optical computation element with other data in a geosteering procedure. At 910, a set of data related to the drilling operation of interest is acquired. This data can include data from one or more measurement techniques. For example, the acquired data can include an acoustic image log, a gamma log, and resistivity data from measurements using different tools. These can include acoustic and electromagnetic tools that examine the formation over a relatively large distance from the borehole. Acquisition of this set of data can include operating these tools to collect the data.

At 920, data from a tool using an optical computation element downhole in the drilling operation is generated. Signals output from detectors of the tool arranged with the optical computation element can be analyzed to generate data regarding the chemical composition near the tool. The tool can typically be disposed near a drill bit in a logging while drilling operation. This arrangement provides data for assessment of the formation near the drilling point.

At 930, the location of the drilling operation relative to the surrounding formation using the acquired data and the generated data is assessed. The chemical data generated from the optical computation element can be combined with image data from other tools for display at the surface to monitor and/or direct the geosteering activity. In addition, the chemical data generated from the optical computation element near the drill bit can be combined with other data, such as resistivity data, relative to regions away from the drill it to provide a indication of which direction to geosteer the well.

At 940, the well is geosteered based on the assessment. The geosteering can include, among other actions, maintaining the well in a desired target region such as a reservoir, directing the well away from regions such as regions with high water content, or directing the well through regions that are easier for the drilling operation to traverse. The geosteering can be controlled from a surface system under the direction of an operator. The geosteering can be controlled by downhole electronics that are arranged to collect the data, make comparisons, and generate control signals to operate the direction of the drill bit using instructions stored in the electronics. The downhole control of the geosteering can be monitored at the surface by an operator.

Figure 10:
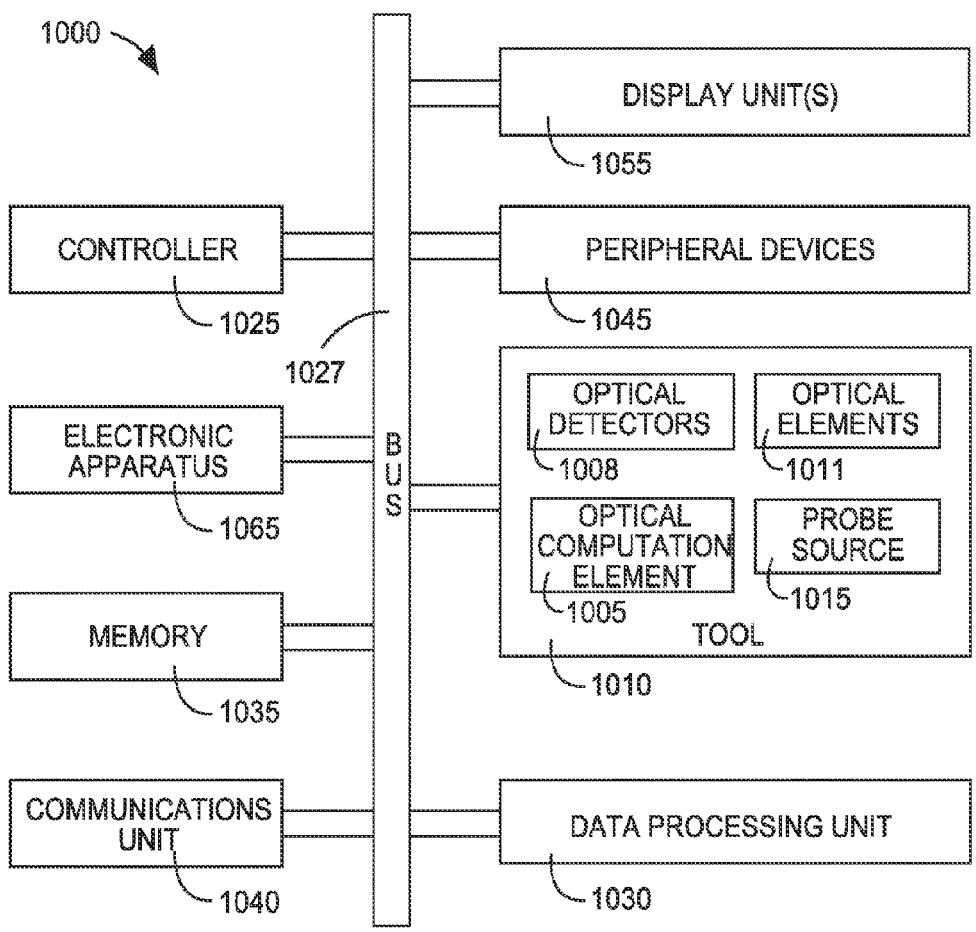
FIG. 10 depicts a block diagram of features of an example system having a tool structured with an optical computation element, in accordance with various embodiments.

FIG. 10 depicts a block diagram of an example embodiment of a system 1000 having a tool 1010 structured with an optical computation element 1005 operable downhole in a well. Tool 1010 can include optical detectors 1008, optical elements 1011, and a probe source 1015 that operate in conjunction with optical computation element 1005. System 1000 can be structured to operate optical computation element 1005 in accordance with the teachings herein. System 1000 can include a controller 1025, a memory 1035, an electronic apparatus 1065, and a communications unit 1040.

Controller 1025, memory 1035, and communications unit 1040 can be arranged to operate as a processing unit to control operation of tool 1010, in a manner similar or identical to the procedures discussed herein. Such a processing unit can be realized using a data processing unit 1030, which can be implemented as a single unit or distributed among the components of system 1000 including electronic apparatus 1065. Controller 1025 and memory 1035 can operate to control activation of probe source 1015 and collection of signals from tool 1010. The collection of signals can include acquisition from optical detectors 1008 to analysis the chemical based data generated by tool 1010 in accordance with measurement procedures and signal processing as described herein. System 1000 can be structured to function in a manner similar to or identical to structures associated with FIGS. 1-9 and 11.

System 1000 can also include a bus 1027, where bus 1027 provides electrical conductivity among the components of system 1000. Bus 1027 can include an address bus, a data bus, and a control bus, each independently structured or in an integrated format. Bus 1027 can be realized using a number of different communication mediums that allows for the distribution of components of system 1000. Communications unit 1040 can include downhole communications operable with bus 1027. Such downhole communications can include a telemetry system. Use of bus 1027 can be regulated by controller 1025.

In various embodiments, peripheral devices 1045 can include additional storage memory and/or other control devices that may operate in conjunction with controller 1025 and/or memory 1035. In an embodiment, controller 1025 is realized as a processor or a group of processors that may operate independently depending on an assigned function. Peripheral devices 1045 can be arranged with one or more displays 1055, as a distributed component on the surface, that can be used with instructions stored in memory 1035 to implement a user interface to monitor the operation of tool 1010 and/or components distributed within system 1000. The user interface can be used to input operating parameter values such that system 1000 can operate autonomously substantially without user intervention.

Figure 11:
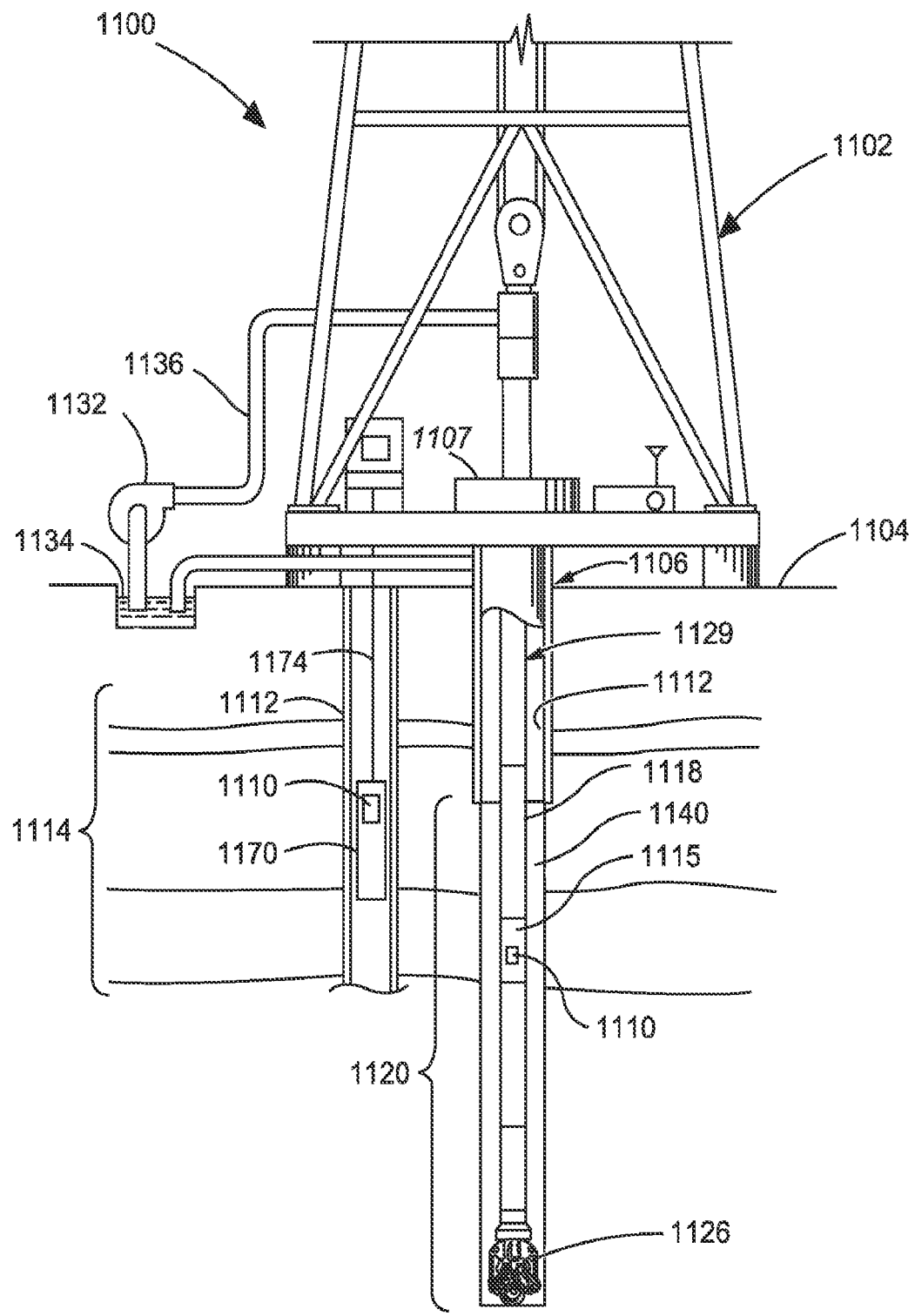
FIG. 11 depicts an example system at a drilling site, where the system includes a tool structured with an optical computation element, in accordance with various embodiments.

FIG. 11 depicts an embodiment of a system 1100 at a drilling site, where system 1100 includes a measurement tool 1110 structured with an optical computation element. System 1100 includes tool 1110 having an optical computation element that can be realized in a similar or identical manner to arrangements discussed herein. System 1100 can include a drilling rig 1102 located at a surface 1104 of a well 1106 and a string of drill pipes, that is, drill string 1129, connected together so as to form a drilling string that is lowered through a rotary table 1107 into a wellbore or borehole 1112. The drilling rig 1102 can provide support for drill string 1129. The drill string 1129 can operate to penetrate rotary table 1107 for drilling a borehole 1112 through subsurface formations 1114. The drill string 1129 can include drill pipe 1118 and a bottom hole assembly 1120 located at the lower portion of the drill pipe 1118.

The bottom hole assembly 1120 can include drill collar 1115, measurement tool 1110 attached to drill collar 1115, and a drill bit 1126. The drill bit 1126 can operate to create a borehole 1112 by penetrating the surface 1104 and subsurface formations 1114.

Measurement tool 1110 can be structured for an implementation in the borehole of a well as a measurements-while-drilling (MWD) system such as a LWD system. Measurement tool 1110 may include optical detectors, optical elements, and a probe source that operate in conjunction with an optical computation element. System 1100 can be structured to operate the optical computation element in accordance with the teachings herein. Measurement tool 1110 can include a data processing unit to analyze signals generated by measurement tool 1110 and provide measurement results from tool 1110 to the surface over a standard communication mechanism for operating a well. Alternatively, measurement tool 1110 can include electronics with a communications interface to provide signals generated by measurement tool 1110 to the surface over a standard communication mechanism for operating a well, where these signals can be analyzed at a processing unit at the surface.

In various embodiments, measurement tool 1110 may be included in a tool body 1170 coupled to a logging cable 1174 such as, for example, for wireline applications. Tool body 1170 can include measurement tool 1110 containing optical detectors, optical elements, and a probe source that operate in conjunction with an optical computation element. System 1100 can be structured to operate the optical computation element in accordance with the teachings herein. Measurement tool 1110 can include a data processing unit to analyze signals generated by measurement tool 1110 and provide measurement results from tool 1110 to the surface over a standard communication mechanism for operating a well. Alternatively, measurement tool 1110 can include electronics with a communications interface to provide signals generated by measurement tool 1110 to the surface over a standard communication mechanism for operating a well, where these signals can be analyzed at a processing unit at the surface Logging cable 1174 may be realized as a wireline (multiple power and communication lines), a mono-cable (a single conductor), and/or a slick-line (no conductors for power or communications), or other appropriate structure for use in bore hole 1112.

During drilling operations, the drill string 1129 can be rotated by the rotary table 1107. In addition to, or alternatively, the bottom hole assembly 1120 can also be rotated by a motor (e.g., a mud motor) that is located downhole. The drill collars 1115 can be used to add weight to the drill bit 1126. The drill collars 1115 also can stiffen the bottom hole assembly 1120 to allow the bottom hole assembly 1120 to transfer the added weight to the drill bit 1126, and in turn, assist the drill bit 1126 in penetrating the surface 1104 and subsurface formations 1114.

During drilling operations, a mud pump 1132 can pump drilling fluid (sometimes known by those of skill in the art as "drilling mud") from a mud pit 1134 through a hose 1136 into the drill pipe 1118 and down to the drill bit 1126. The drilling fluid can flow out from the drill bit 1126 and be returned to the surface 1104 through an annular area 1140 between the drill pipe 1118 and the sides of the borehole 1112. The drilling fluid may then be returned to the mud pit 1134, where such fluid is filtered. In some embodiments, the drilling fluid can be used to cool the drill bit 1126, as well as to provide lubrication for the drill bit 1126 during drilling operations. Additionally, the drilling fluid may be used to remove subsurface formation 1114 cuttings created by operating the drill bit 1126.

In various embodiments, a machine-readable storage device, such as a computer-readable storage device, has machine-executable instructions, which when executed by a controller, such as a processor, cause a measurement tool to operate downhole in a well using an optical computation element. These instructions provide a mechanism for the measurement tool to operate in a manner similar to or identical to a measurement having an optical computation element associated with FIGS. 1-11. The machine-readable storage device is not limited to any one type of device. Further, a machine-readable storage device, herein, is a physical device that stores data represented by physical structure within the device. Machine-readable storage devices may include, but are not limited to, solid-state memories, optical devices, and magnetic devices. Examples of machine-readable storage devices include, but are not limited to, read only memory (ROM), random access memory (RAM), a magnetic disk storage device, an optical storage device, a flash memory, and other electronic, magnetic, and/or optical memory-like devices.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A method comprising:
    directing light from a borehole wall to an optical computation element, the optical computation element being an optical device that performs a computation in the optical domain on received light in an interaction with the received light;
    analyzing light output from the optical computation element in response to the optical computation element receiving the light from the borehole wall; and
    determining a property associated with the borehole wall from analyzing the light output from the optical computation element.

2. The method of claim 1, wherein the method includes generating a signal to direct a drilling operation based on the determined property.

3. The method of claim 2, wherein generating the signal to direct the drilling operation includes geosteering the drilling operation.

4. The method of claim 3, wherein geosteering the drilling operation includes maintaining the borehole within a reservoir pay zone.

5. The method of claim 2, wherein generating the signal to direct the drilling operation includes generating a monitoring signal to provide advanced warning with respect to a safety condition of the drilling operation.

6. The method of claim 1, wherein determining the property associated with the borehole wall includes determining one or more of a porosity of the borehole wall, a composition of the borehole wall, or a formation fluid measurement corresponding to the borehole wall.

7. The method of claim 1, wherein the method includes generating probe light directed at the borehole wall such that redirection of the probe light from the borehole wall provides the light directed from the borehole wall to the optical computation element.

8. The method of claim 7, wherein generating the probe light includes using a probe device such that the probe device physically contacts the borehole wall and the probe light passes from the probe device to the borehole wall.

9. The method of claim 8, wherein the method includes scraping off material from the borehole wall using the probe device.

10. The method of claim 7, wherein generating the probe light includes transmitting the probe light from a source, disposed in a tool containing the optical computation device, through a fluid to the borehole wall.

11. The method of claim 1, wherein the method includes determining values of the property associated with the borehole wall as a tool, on which the optical computation device is disposed, moves along a length of the borehole; and generating a two-dimensional map of the borehole wall from the values.

12. The method of claim 11, wherein the method includes monitoring contamination within a drilling fluid from analyzing the light output from the optical computation element at a frequency of light, in the light directed to the optical computation element, for which the drilling fluid is transparent.

13. A method comprising:
    using one or more optical computation elements to determine an optical characteristic of a drilling fluid within a drillstring of a drilling operation, the optical computation element being an optical device that performs a computation in the optical domain on received light in an interaction with the received light;
    using the one or more optical computation elements to determine an optical characteristic of a fluid within an annulus of the drillstring, the annulus of the drillstring being a space between the drillstring and a wellbore wall; and
    monitoring a difference between the optical characteristic of the drilling fluid and the optical characteristic of the fluid within the annulus.

14. The method of claim 13, wherein the method includes measuring fluids leaking into a formation due to drilling at a drill bit location in the drilling operation.

15. The method of claim 13, wherein the method includes using only one optical computation element.

16. The method of claim 13, wherein the method includes determining a property associated with the fluid within the annulus based on monitoring the difference between the optical characteristic of the drilling fluid and the optical characteristic of the fluid within the annulus; and generating a signal to direct a drilling operation based on the determined property.

17. The method of claim 16, wherein generating the signal to direct the drilling operation includes geosteering the drilling operation or generating a monitoring signal to provide advanced warning with respect to a safety condition of the drilling operation.

18. A non-transitory machine-readable storage device having instructions stored thereon, which, when performed by a machine, cause the machine to perform operations, the operations comprising:
    directing light from a borehole wall to an optical computation element, the optical computation element being an optical device that performs a computation in the optical domain on received light in an interaction with the received light;

analyzing light output from the optical computation element in response to the optical computation element receiving the light from the borehole wall; and determining a property associated with the borehole wall from analyzing the light output from the optical computation element.

19. The non-transitory machine-readable storage device of claim 18, wherein the operations include generating a signal to direct a drilling operation based on the determined property.

20. The non-transitory machine-readable storage device of claim 19, wherein generating the signal to direct the drilling operation includes geosteering the drilling operation.

21. The non-transitory machine-readable storage device of claim 20, wherein geosteering the drilling operation includes maintaining the borehole within a reservoir pay zone.

22. The non-transitory machine-readable storage device of claim 20, wherein generating the signal to direct the drilling operation includes generating a monitoring signal to provide advanced warning with respect to a safety condition of the drilling operation.

23. The non-transitory machine-readable storage device of claim 18, wherein determining the property associated with the borehole wall includes determining one or more of a porosity of the borehole wall, a composition of the borehole wall, or a formation fluid measurement corresponding to the borehole wall.

24. The non-transitory machine-readable storage device of claim 18, wherein the operations include determining values of the property associated with the borehole wall as a tool, on which the optical computation device is disposed, moves along a length of the borehole; and generating a two-dimensional map of the borehole wall from the values.

25. The non-transitory machine-readable storage device of claim 24, wherein the operations include monitoring contamination within a drilling fluid from analyzing the light output from the optical computation element at a frequency of light, in the light directed to the optical computation element, for which the drilling fluid is transparent.

26. A system comprising:
an optical computation element disposed in a housing, the housing attachable to a drillstring, the optical computation element being an optical device that performs a computation on received light in the optical domain in an interaction with the received light;

a window in the housing arranged to receive light from exterior to the housing such that the light is directed from a region, exterior to the drillstring, to the optical computation element when the housing is mounted on the drillstring; and an analysis unit structured to provide a signal based on an output from the optical computation element in response to the optical computation element receiving the light from exterior to the drillstring, the signal provided to direct a drilling operation based on a property of the region determined from the output from the optical computation element.

27. The system of claim 26, wherein the system further comprises an optical source to generate light that is reflected from exterior to the housing such that the reflected light provides the received light directed to the optical computation element.

28. The system of claim 27, wherein the system includes an additional window structured such that the generated light by the optical source, with the optical source disposed in the housing, exits the housing to reflect from exterior to the housing.

29. The system of claim 26, wherein the system includes a probe device structured to generate a probe light, the probe device physically arranged on the housing to contact a borehole wall such that probe light passed from the probe device to the borehole wall provides the received light from exterior to the housing.

30. The system of claim 29, wherein the probe device is operable to scrap off material from the borehole wall.

31. The system of claim 26, wherein the system includes optical detectors arranged relative to the optical computation element to detect light directed from the optical computation element to a respective optical detector.

32. The system of claim 31, wherein the arrangement of optical detectors are coupled with the analysis unit to provide signals to the analysis unit, the analysis unit structured to determine a difference between a drilling fluid within a drillstring of a drilling operation and a fluid within an annulus of the drillstring based on the signals.

\* \* \* \* \*